(12) United States Patent
Calco et al.

(10) Patent No.: US 7,674,234 B2
(45) Date of Patent: Mar. 9, 2010

(54) CERVICAL COLLAR WITH GEARED ADJUSTMENT

(75) Inventors: Wayne A. Calco, Laguna Hills, CA (US); David Laurence Moeller, Tustin, CA (US); Jozsef Horvath, Fullerton, CA (US); Geoffrey Garth, Long Beach, CA (US)

(73) Assignee: Carsar, LLC

( * ) Notice: Subject to any disclaimer, the term of this patent is extended or adjusted under 35 U.S.C. 154(b) by 1258 days.

(21) Appl. No.: 11/194,006

(22) Filed: Jul. 28, 2005

(65) Prior Publication Data

US 2007/0027418 A1 Feb. 1, 2007

(51) Int. Cl.
*A61F 5/00* (2006.01)
(52) U.S. Cl. .................................. 602/18; 128/DIG. 23
(58) Field of Classification Search ............. 602/17–19; 128/DIG. 23
See application file for complete search history.

(56) References Cited

U.S. PATENT DOCUMENTS 2,791,999 A * 5/1957 Bustamante ................. 601/39
5,005,563 A * 4/1991 Veale ........................... 602/18
5,688,229 A * 11/1997 Bauer .......................... 602/18
5,865,773 A * 2/1999 Koledin ....................... 602/18
6,423,020 B1 * 7/2002 Koledin ....................... 602/18
2004/0204666 A1 10/2004 Marsh

* cited by examiner

*Primary Examiner*—Michael A. Brown
(74) *Attorney, Agent, or Firm*—Fish & Associates PC

(57) ABSTRACT

The present invention provides a cervical collar with a rack and pinion adjustment mechanism. The rack moves a chin support member, which raises and lowers a chin piece. Independently, the present invention provides methods and mechanisms in which the chin support can angulate independently of the collar body. Such angulation is preferably accomplish by pivotally supporting the chin piece on the racks, or on the left and right chin support pieces. Thus, in a preferred class of embodiments, the collar has a pivot for the chin support pieces relative to the collar body, and an other pivot for the chin piece relative to the chin support pieces.

13 Claims, 4 Drawing Sheets

US 7,674,234 B2

CERVICAL COLLAR WITH GEARED ADJUSTMENT

FIELD OF THE INVENTION

The field of the invention is cervical collars.

BACKGROUND OF THE INVENTION

Cervical collars are generally used to maintain a spine in neutral alignment. In order to maintain neutral alignment, the user's chin must be supported at a particular position. Because of this requirement for neutral alignment, and because users of the collars are proportioned differently, collars are made in various sizes. One of the problems with making collars in various sizes, however, is that medical practitioners have to stock and keep track of a multitude of sizes, which can become quite burdensome.

In order to address the burden caused by the need to stock various sizes, adjustable collars have emerged. One more recent patent, U.S. Pat. No. 6,663,581 to Calabrese, teaches a collar that can be adjusted by manually sliding a mandible into position and then inserting a clip to lock it. While the Calabrese collar may have addressed the adjustability problem with a modicum of success, there are still problems with the way the adjustment is done. One problem is that previously known adjustable collars have independently adjusted left and rights sides, which allows for asymmetric adjustments. Another problem is that making left and right adjustments requires two adjustments rather than one. Still a third problem is that failure of the adjustment on a single side to hold in position may result in a significant torquing of the head and lead to significant misalignment of the cervical spine.

A separate set of problems with respect to prior art cervical braces is that the chin support piece is rigidly coupled to the collar body, and does not sufficiently allow for different shaped chins. The result is that a wearer can experience excessive pressure at localized regions of the chin. This is not so much of a problem for an emergency collar, but it a very significant problem for a collar intended for extended wear.

Thus, there is a need for an adjustable collar where left and rights sides can be adjusted with a single motion, and that provides a chin support that can angulate independently of the collar body.

SUMMARY OF THE INVENTION

The present invention provides methods and mechanisms in which left and rights sides can be adjusted with a single motion. Adjustment of the left and rights sides can be advantageously accomplished using a gear mechanism, and in particular a rack and pinion mechanism. As the pinion is rotated, the chin support member is raised or lowered as a result of movement of the racks.

Independently, the present invention provides methods and mechanisms in which the chin support can angulate independently of the collar body. Such angulation is preferably accomplish by pivotally supporting the chin piece on the racks, or on the left and right chin support pieces. Thus, in a preferred class of embodiments, the collar has a pivot for the chin support pieces relative to the collar body, and another pivot for the chin piece relative to the chin support pieces.

Various objects, features, aspects and advantages of the present invention will become more apparent from the following detailed description of preferred embodiments of the invention, along with the accompanying drawings in which like numerals represent like components.

DETAILED DESCRIPTION

Figure 1:
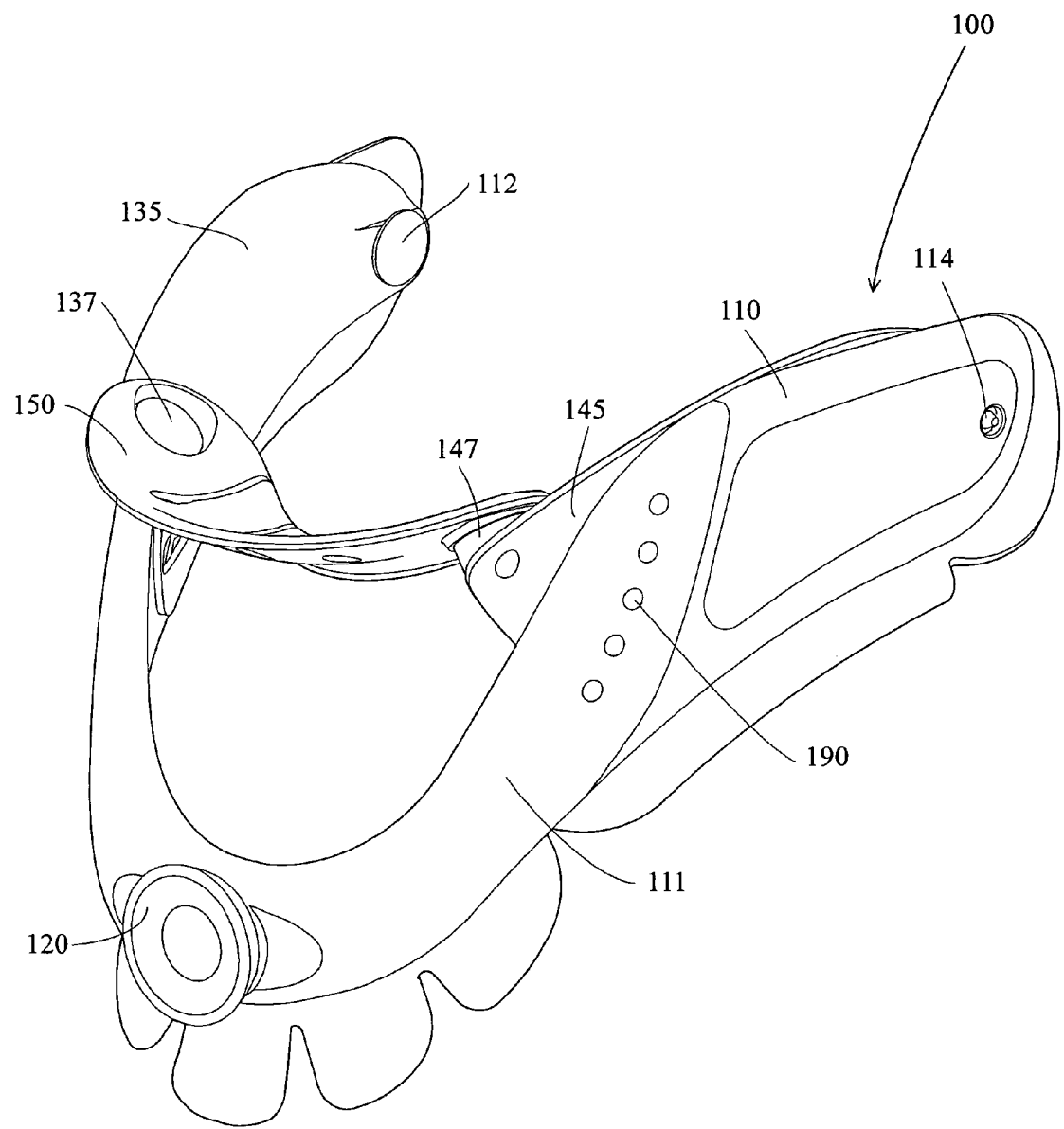
FIG. 1 is a front perspective view of a cervical collar.

Referring first to FIGS. 1-4, a cervical collar 100 comprises a main collar body 110, mechanism enclosure 111, a knob 120, a first rack 130, a second rack 140, a first chin support member 135, a second chin support member 145, and a chin piece 150.

First and second racks 130, 140 and the pinion gear 310 cooperate to adjust the height of the first and second chin support member 135. 145, and thereby the height of the chin piece 150. These parts are configured to allow use of a single (or relatively small number of collars) to maintain the head and neck in neutral alignment, supports must be consistent with the key dimension of an individual wearer. As used herein, the term "key dimension" means the height of the inferior surface of the chin where the chin piece supports the chin, relative to a horizontal line drawn at the top of the shoulder where the collar body rests upon the trapezius muscles.

As best seen in FIG. 1, the racks 130, 140 are guided between the main collar body 110 and mechanism retainer 370 toward the pinion gear 310. The pins 132 and 142 couple the racks to the chin support members 135 and 145 such that upward movement of a rack causes the associated chin support member to also move upward. Likewise, downward movement of a rack will cause the associated chin support member to move downward. Because the racks 130, 140 are used to push the chin support members 135, 145 upward relative to collar body 110 (and of course also relative to the wearer's sternum and shoulders), they are preferably made of a sufficiently stiff material. Contemplated materials include hard thermoplastic, metal, etc.

Pinion gear 310 is preferably constructed from a relatively hard plastic or other suitable material that exhibits relatively little wear over time due to contact with the rack teeth (e.g. acetyl resin). The teeth of the pinion gear must of course mate with the teeth of the racks.

In the embodiment of FIGS. 1-4, the height adjustment is accomplished by rotating knob 120, which causes rotation of a pinion gear (see 310 in FIG. 3), which moves the racks 130, 140 laterally and vertically, which causes the first and second chin support members 135, 145 to move up and down. Rotation of the knob 120, and hence of the gear 310, is preferably bi-directional with one direction (e.g. clockwise) causing the racks 130, 140 to move upward and he other (e.g. counterclockwise) causing the racks to move downward.

Figure 2:
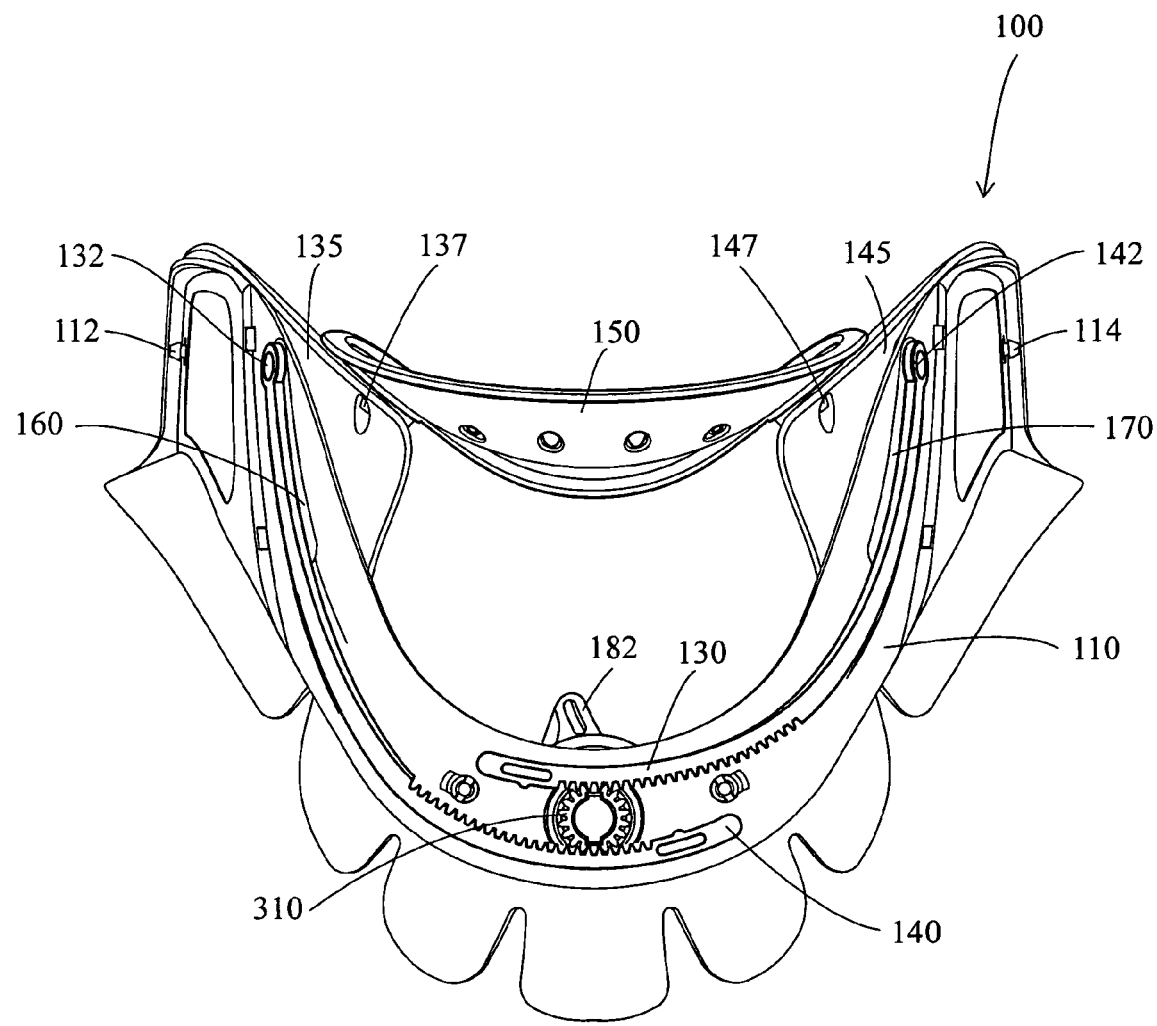
FIG. 2 is a front view of the cervical collar of FIG. 1, with the cover removed.
Figure 3:
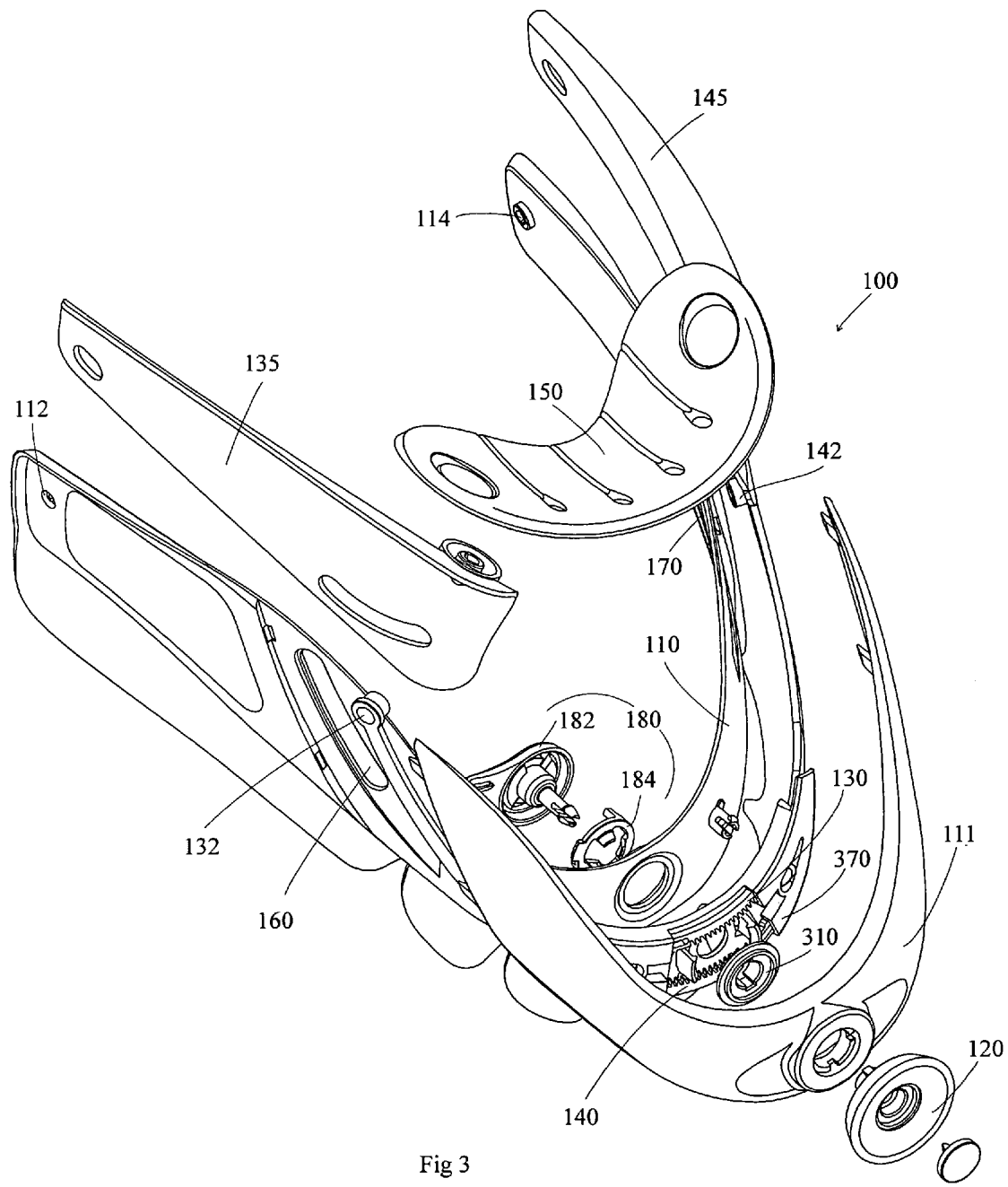
FIG. 3 is an exploded perspective view of a cervical collar of FIG. 1.

Since the pinion gear 310 operates upon both racks 130, 140 simultaneously, each chin support member 135, 145 moves up or down at the same time, at the same rate, and for the same distance. Preferred embodiments include some mechanism for limiting the travel of the racks 130, 140 and support members 135, 145. This can be accomplished in several ways. For example, travel of the racks 130, 140 can be readily limited by limiting rotation of the pinion gear 310, through the use of stops, by limiting the number of teeth on one or both of the racks 130, 140, and/or limiting the rise of the chin support member 135, 145 such as through the use of a pin within a slot. FIGS. 1 and 2 show the use of pins 132, 142 cooperation with slots 160, 170 for this purpose. Slots 160 and 170 allow the support members 135, 145 to move from a fully extended configuration in which the pins 132, 142 are at their highest point to a fully compressed configuration in which the pins 132, 142 are at their lowest point. The fully extended configuration is intended to adapt to a person with a large key dimension (tall neck), while the most compressed configuration is intended to adapt to a person with an especially small key dimension (short neck).

It should also be appreciated that the extent of pivoting of the chin piece 150 should probably be limited in some manner to prevent excessive angulation that could result in the wearer's chin sliding off the chin piece. Such limitation can be provided by the shapes of the juxtaposing surfaces of the chine piece 150 and the side pieces 135, 145.

Preferred embodiments of collar 100 can be readily sized to a wearer by including calibration markings 190 that correspond to key dimensions. For example, a calibration marking for a "short" collar might correspond to a key dimension of 0.75. The calibration can be in a relatively small unit of measure such as a millimeter but is more likely to be in centimeters, inches or some other designation. Placement of the calibration markings 190 should be conspicuous to the person setting the size (generally not the user himself). In FIG. 1, for example, the calibration markings 190 are shown on the side of the collar body. In other embodiments, the calibration may be on or around the knob or some other place along the path of either rack.

Knob 120 not only rotates, but also move in and out. In the fully inward configuration the knob is locked from rotation, and in the outward configuration the knob 120 is rotatable (unlocked). In the particular embodiments shown, the pinion gear 310 is directly connected to the knob 120, and the knob 120 is biased to the locked (inward) position.

A safety 180, comprising lock 182 and spring 184, can optionally be provided as a secondary means of prohibiting movement of the racks. Safety 180 can operate in any suitable fashion, but in this particular embodiment the safety 180 prevents the knob 120 from moving to the outward (rotatable) position. This may be done by providing a tab on the pinion gear which can be stopped by contact with the safety.

Chin support members 135 and 145 are pivotally mounted to the main collar body 110 at points 112 and 114. Additionally, chin piece 150 is pivotally mounted to the chin support members 135 and 145 at pivots 137, 147. As used herein the term pivot includes mechanisms that provide pivoting motion, even though there is no actual axle or line about which the pivoting motion takes place. Thus, chin piece 150 can be said to be pivotally mounted to the chin support members 135 and 145 at pivots 137, 147 even in situations where these parts are molded together in a manner that provides sufficient "play" to effectively provide a pivoting type motion.

Figure 4:
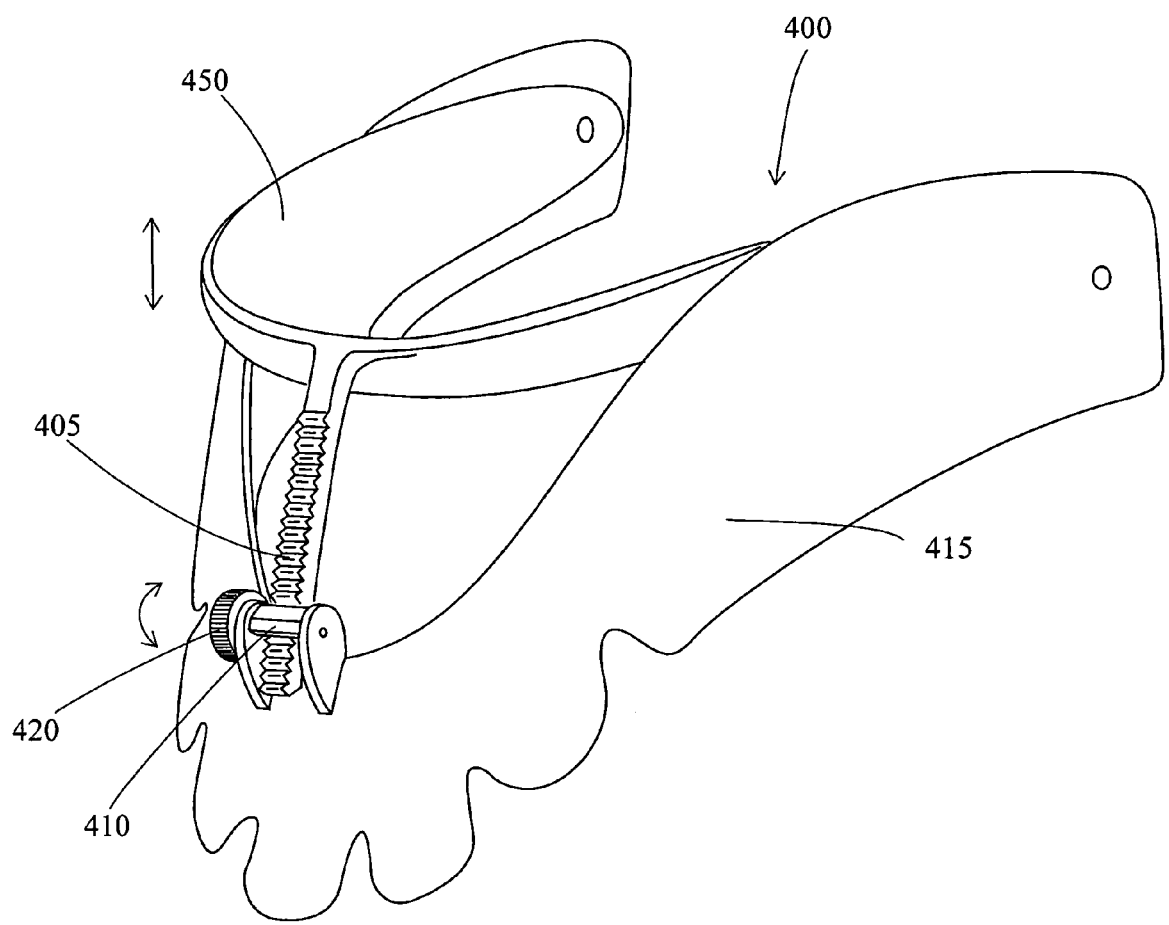
FIG. 4 is a perspective view of an alternative cervical collar utilizing a single rack.

An alternative embodiment of a cervical collar 400 is shown in FIG. 4. The collar 400 has a single central rack 405 and a pinion gear 410 attached to main collar body 415. Rotation of the pinion gear 410 moves rack 405 upward, which therefore raises chin piece 450. As with the embodiment of FIGS. 1-3, the height of the chin piece 450 can be adjusted by rotating a knob 420, which turns the pinion gear 410. In this embodiment, however, there is no need to pull out the knob.

It should also be appreciated that the terms "rack" and "pinion" are used herein in a broader manner than ordinary usage, and include embodiments with teeth of any size, or indeed no teeth at all. In the latter case, for example, the rack and pinion can each have rubbery surface that together provide sufficient friction to couple the relatively motions of the rack and pinion. Moreover, in common usage one often refers to the rack portion of a rack and pinion as being flat. As used in this application, a rack need not be flat, and indeed in most instances will be curved. The only essential feature of the racks and pinions as used herein is that the rack translates in space as the pinion rotates. Where discussion is limited to a toothed rack and pinion, either the teeth are expressly stated, or the pinion is referred to as a pinion gear.

Thus, specific embodiments and applications of a cervical collar with a geared adjustment have been disclosed. It should be apparent, however, to those skilled in the art that many more modifications besides those already described are possible without departing from the inventive concepts herein. The inventive subject matter, therefore, is not to be restricted except in the spirit of the appended claims. Moreover, in interpreting both the specification and the claims, all terms should be interpreted in the broadest possible manner consistent with the context. In particular, the terms "comprises" and "comprising" should be interpreted as referring to elements, components, or steps in a non-exclusive manner, indicating that the referenced elements, components, or steps may be present, or utilized, or combined with other elements, components, or steps that are not expressly referenced.

What is claimed is:

1. A cervical collar having a chin piece, a collar body, and a chin height adjustment mechanism comprising a first rack that cooperates with a pinion, disposed such that a single adjustment to the adjustment mechanism operates to raise both lateral sides of the chin piece relative to the collar body.

2. The cervical collar of claim 1, further comprising a second rack that cooperates with the pinion.

3. The cervical collar of claim 2, wherein at least one of the racks and the pinion has teeth.

4. The cervical collar of claim 1, wherein the rack is coupled to a lateral chin support member.

5. The cervical collar of claim 4, wherein rotational movement of the pinion is bi-directional, one direction causing the lateral chin support member to raise and another direction causing the chin support member to lower.

6. The cervical collar of claim 4, wherein the lateral chin support member is coupled to a chin piece.

7. The cervical collar of claim 1, wherein the chin piece raises and lowers as a result of movement of the rack.

8. The cervical collar of claim 1, further comprising a chin support piece, and wherein the chin piece rotates relative to the chin support piece, and the chin support piece rotates relative to the cervical collar body.

9. The cervical collar of claim 1, further comprising a chin support piece that moves up and down, the chin piece rotating relative to the chin support piece.

10. The cervical collar of claim 1, further comprising a knob that is effective to raise and lower the chin piece, and is configurable between an inward configuration in which rotation of the pinion is locked and an outward configuration in which rotation of the pinion is unlocked.

11. The cervical collar of claim 1, further comprising a safety that substantially prohibits rotation of the pinion.

12. The cervical collar of claim 1, wherein the rack and the pinion have alternating peaks and valleys that cooperate with each other to move the rack.

13. The cervical collar of claim 1, further comprising a calibration that correlates with a height of the chin piece.

* * * * *